US012226282B2

United States Patent
Thomé et al.

(10) Patent No.: US 12,226,282 B2
(45) Date of Patent: Feb. 18, 2025

(54) DENTAL TOOL, PROSTHETIC COMPONENT, AND TOOL AND COMPONENT ASSEMBLY

(71) Applicant: JJGC INDÚSTRIA E COMÉRCIO DE MATERIAIS DENTÁRIOS S.A., Curitiba (BR)

(72) Inventors: Geninho Thomé, Curitiba (BR); Felix Andreas Mertin, Curitiba (BR); Rafael Calixto Salatti, Curitiba (BR); Ilderaldo Jose Lucca, Curitiba (BR)

(73) Assignee: JJGC INDÚSTRIA E COMÉRCIO DE MATERIAIS DENTÁRIOS S.A., Curitiba (BR)

( * ) Notice: Subject to any disclaimer, the term of this patent is extended or adjusted under 35 U.S.C. 154(b) by 48 days.

(21) Appl. No.: 16/640,433

(22) PCT Filed: Aug. 23, 2018

(86) PCT No.: PCT/BR2018/050302
§ 371 (c)(1),
(2) Date: Apr. 27, 2020

(87) PCT Pub. No.: WO2019/036788
PCT Pub. Date: Feb. 28, 2019

(65) Prior Publication Data
US 2020/0281696 A1 Sep. 10, 2020

(30) Foreign Application Priority Data
Aug. 23, 2017 (BR) .......................... 102017018084-0
Jul. 6, 2018 (BR) .......................... 102018013941-0

(51) Int. Cl.
*A61C 8/00* (2006.01)
*A61C 13/08* (2006.01)
*B25B 15/00* (2006.01)

(52) U.S. Cl.
CPC ............ *A61C 8/0089* (2013.01); *A61C 13/08* (2013.01); *B25B 15/005* (2013.01)

(58) Field of Classification Search
CPC ....... A61C 8/0089; A61C 8/005; A61C 13/12; A61C 13/2255; A61C 13/273; A61C 13/275; B25B 15/005; B25B 15/00
See application file for complete search history.

(56) References Cited

U.S. PATENT DOCUMENTS 4,306,865 A * 12/1981 Leonard ................... F16H 1/28
433/104
2006/0266168 A1* 11/2006 Pacheco, Jr. .......... B25B 13/065
81/460

(Continued)

FOREIGN PATENT DOCUMENTS

BR MU8401655 U 3/2006
BR 102013027205 A2 9/2014

(Continued)

OTHER PUBLICATIONS

Besegai, Interference Screw For Fixing Ligament, Has Inner Channel With Grooves And Flutes Which Are Oriented Longitudinally And Distributed Uniformly Along Surface Of Inner Channel Which Extends Through Another Channel Emerging At Level Of Point, English Translation, 2006 (Year: 2006).*

(Continued)

*Primary Examiner* — Cris L. Rodriguez
*Assistant Examiner* — Sydney J Pulvidente
(74) *Attorney, Agent, or Firm* — Oliff PLC

(57) ABSTRACT

A dental tool and prosthetic components/screws that allow capturing, transporting and applying torque so as to perform dental service with a single tool specially adapted for components/screws with reduced dimensions, such as, e.g., smaller than 1.4 mm in diameter.

9 Claims, 16 Drawing Sheets

(56) References Cited

U.S. PATENT DOCUMENTS

| | | | | |
|---|---|---|---|---|
| 2006/0278049 A1* | 12/2006 | Baynham | ............... | F16B 23/003 |
| | | | | 81/436 |
| 2007/0037121 A1* | 2/2007 | Carter | ................... | A61C 8/0089 |
| | | | | 433/173 |
| 2012/0244497 A1* | 9/2012 | Huwais | ................. | A61C 8/0089 |
| | | | | 433/165 |
| 2014/0186797 A1* | 7/2014 | Haus | .................... | A61C 8/0001 |
| | | | | 433/173 |
| 2015/0250565 A1* | 9/2015 | Gustafsson | .......... | A61C 8/0089 |
| | | | | 433/165 |
| 2017/0095909 A1* | 4/2017 | Chen | ..................... | B25B 15/005 |
| 2018/0003241 A1* | 1/2018 | Goss | ..................... | B25B 15/004 |
| 2019/0152033 A1* | 5/2019 | Kukucka | ............... | B25B 15/008 |

FOREIGN PATENT DOCUMENTS

| | | | |
|---|---|---|---|
| EP | 0928165 B1 | 9/2003 | |
| EP | 2 607 722 A1 | 6/2013 | |
| FR | 2879915 A1 * | 6/2006 | ......... A61B 17/8615 |
| WO | 98/12982 A1 | 4/1998 | |
| WO | 02/080804 A1 | 10/2002 | |
| WO | WO-2012007119 A1 * | 1/2012 | ........... A61C 8/0048 |

OTHER PUBLICATIONS

Nov. 13, 2018 International Search Report issued in International Patent Application No. PCT/BR2018/050302.

* cited by examiner

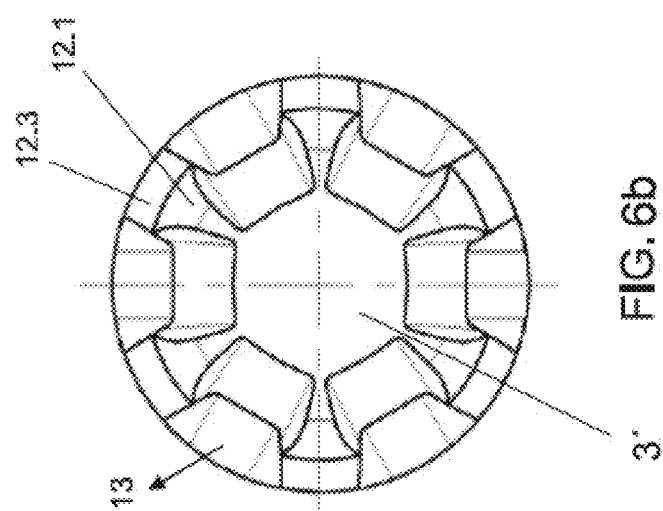
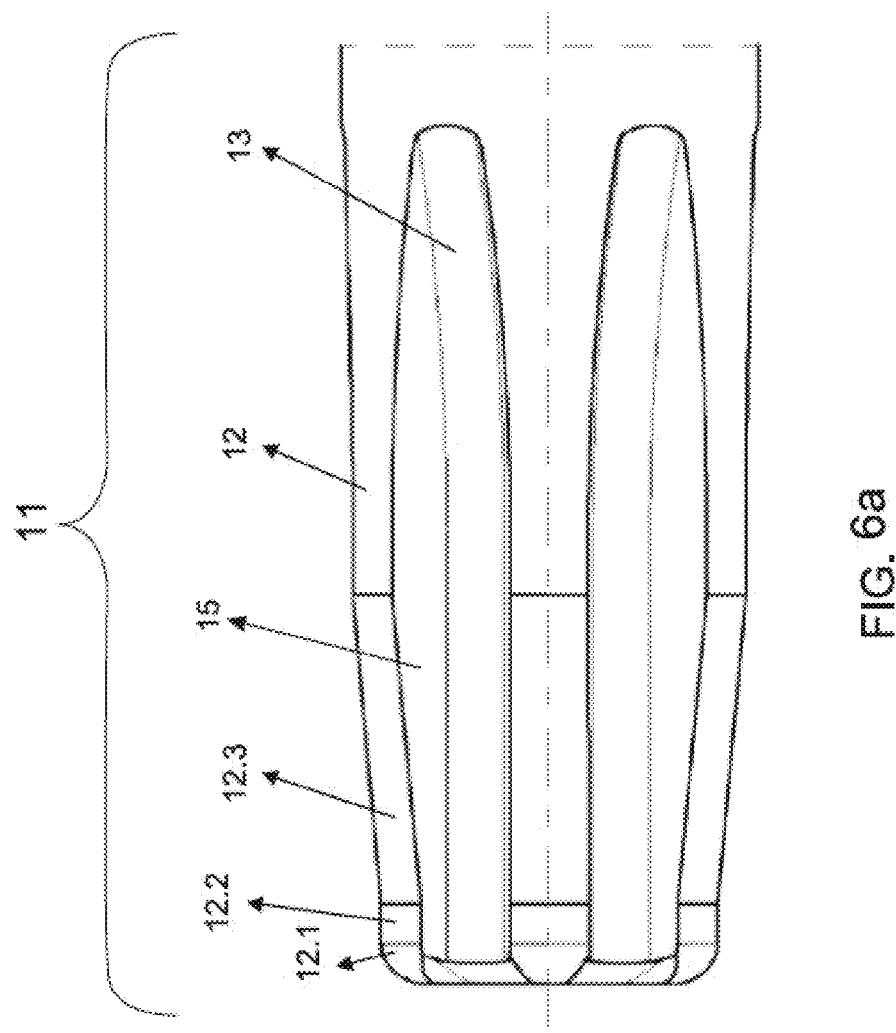

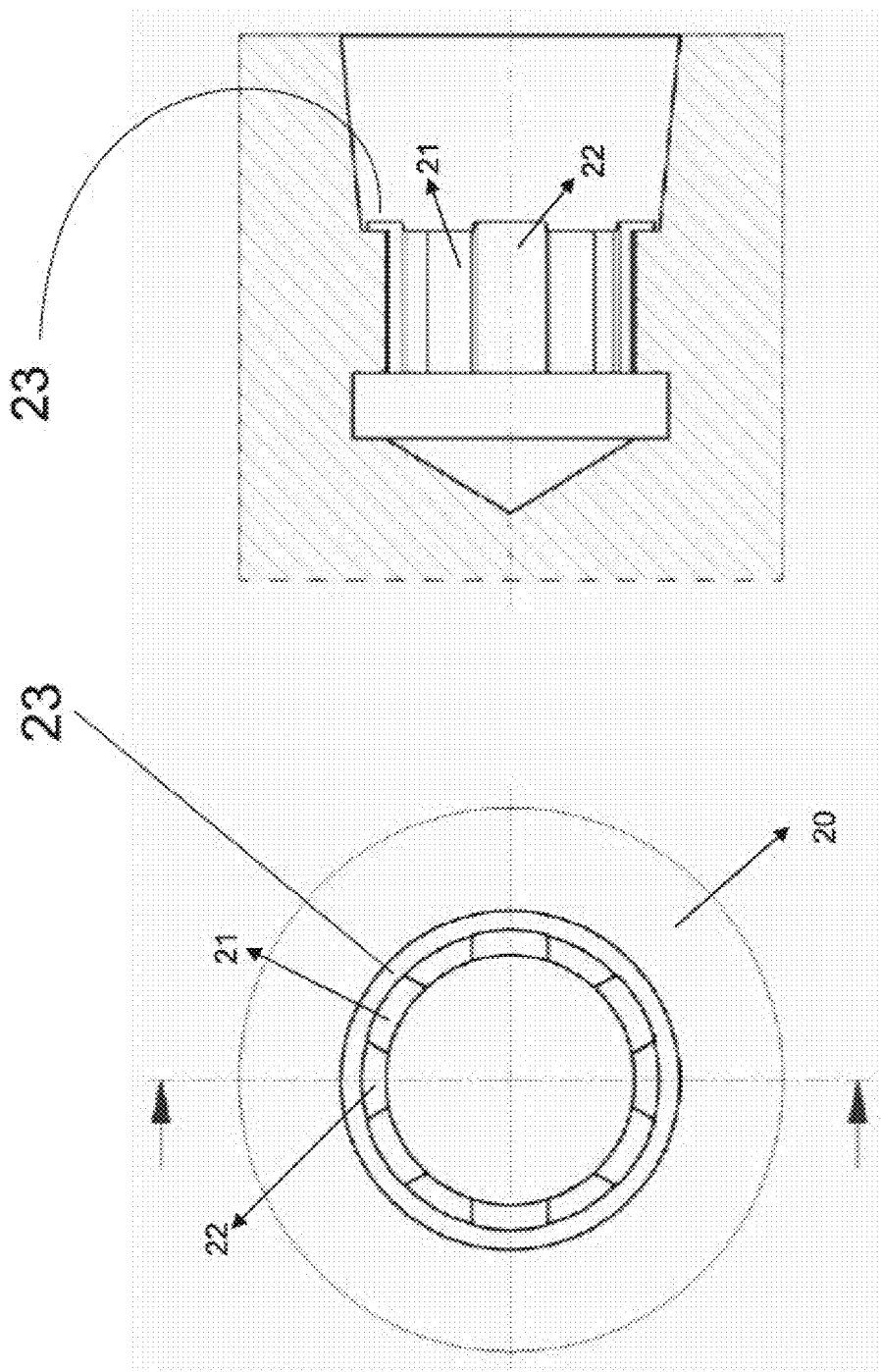

DENTAL TOOL, PROSTHETIC COMPONENT, AND TOOL AND COMPONENT ASSEMBLY

The present invention relates to a tool for capturing, transporting and fixing dental prosthetic components and screws. Specifically, the present invention relates to a wrench for capturing and fixing screws (prosthetic components) in dental implants.

RELATED ART

After installing an implant in a patient's mouth, the dentist must install/fix a component, onto which the dental prosthesis will be installed.

However, as each patient has a different anatomy, the dentist must test various types of prosthetic components until finding the most suitable for the treatment case.

Thus, when carrying out tests, the dentist must use a capture tool (wrench) to transport the prosthetic component from the component case to the patient's mouth. It is essential that this transport occurs safely, mainly because these components are extremely small and easily lost should they fall. Furthermore, for hygienic reasons, if the component is found, it can no longer be used for testing, as it must be sterilized again.

Thus, there is a need for a wrench that can safely capture and transport the component.

To achieve this object, the tools available in the state of the art such as, e.g., the ones illustrated in FIGS. 1 and 2 include a cone shape end, which allows for temporary fastening of the component for transport to the installation site.

After this testing process and finding the suitable component for fastening the implant located in the patient's mouth, the dentist needs to fix the screw. For such, a ratcheting torque wrench is used, which is different from the transport wrench, performing the torque necessary to hold the component in the implant.

It is often necessary to switch tools, as the cone in the torque wrench is used only to temporarily fasten the component to the wrench, preventing the tip of the wrench from fully penetrating the component, i.e. the tip of the wrench is not in contact with the entire internal surface of the component (see FIGS. 1 and 2).

Thus, when the dentist performs torque, the component will be deformed (dilation of the screw head).

Thus, in order to avoid this defect, the wrench used to fasten the component in the implant must have a straight end (tip), i.e., without the cone, allowing the whole tip of the wrench to fully penetrate the internal length of the screw. As a result, when torque is performed, said deformation will not occur.

However, the need to switch tools is cumbersome to dentists. Consequently, many professionals choose to use their own capture wrench to provide torque, deforming the screw.

Furthermore, torque wrenches are typically hexagonally shaped. Due to this shape, the wrench contact area with the component is reduced. If by mistake the dentist delivers more torque than necessary for fixing the screw, deformation of the ridges of the wrench and dilation of the screw head are likely to occur.

This constant deformation, dilating the head of the component and the ridges of the tool, causes the wrench to not fit properly to the component head at certain moments, making rotation impossible in order to tighten the prosthetic component/screw, i.e., the tool slips from the fitting area, spinning on its own. This problem is very common, especially in components with smaller diameters and that require less torque.

In order to prevent the above, there was an attempt to solve such problems, as can be seen in prior art EP0928165B1, which describes an arrangement to be used with a variety of dental screws.

Said document describes a tool (or wrench) with a circular cross section wherein the outer ends of the section widen slightly conically. At the same time, these conical outer ends are fastened to the component surface essentially in parallel.

Thus, the tool described in said document has two functions, the first function being the tightening function, i.e., the ability to provide torque to fasten the component, and the second function being the ability to fasten the tool in the component; the tool's capture ability. Furthermore, it is described that the first and second functions are mechanically separated.

However, although the tool, as presented, has both capture and fastening functions, it is clear from said document that said tool is not applicable to smaller prosthetic components/screws, i.e., usually smaller than 1.4 mm (ranging from 1.4 to 2.5 mm), such that components/screws smaller in diameter cannot benefit from using said tool.

OBJECT OF THE INVENTION

Therefore, the present invention aims to solve the problems presented in the prior art by providing a dental tool (wrench) with both capture and fixation functions, and that can also be used with components/screws with reduced diameters (e.g., smaller than 1.4 mm).

BRIEF DESCRIPTION OF THE INVENTION

The present invention relates to a dental tool for coupling to prosthetic components comprising, at its lower end, a plurality of protrusions and a plurality of recesses, wherein the plurality of protrusions and the plurality of recesses are alternately arranged, each of the protrusions being divided into a first region, a second parallel region, and a third conical region.

Furthermore, the present invention relates to a prosthetic component comprising, on its internal surface, a plurality of counterbores and a plurality of projections, wherein the plurality of recesses and the plurality of projections are alternately arranged.

The invention further presents a set comprising the dental tool and the prosthetic component, such that the plurality of protrusions fits the plurality of counterbores, and the plurality of recesses fits the plurality of projections.

BRIEF DESCRIPTION OF THE DRAWINGS

The present invention will now be described in more detail based on an example implementation illustrated in the drawings. The FIGS. show:

FIG. 6a—side view of the end of a first embodiment of the dental tool herein;

FIG. 6b—front view of the lower end of a first embodiment of dental tool;

FIG. 9a—top view of the prosthetic component/screw of FIG. 8a;

FIG. 9b—side sectional view of the coupling region of the prosthetic component/screw of FIG. 8a;

FIG. 10a—top view of the prosthetic component/screw of FIG. 8b;

FIG. 10b—a side sectional view of the coupling region of the prosthetic component/screw of FIG. 8b;

FIG. 15b—enlarged detailed view of FIG. 15a.

DETAILED DESCRIPTION OF THE DRAWINGS

Figure 1:
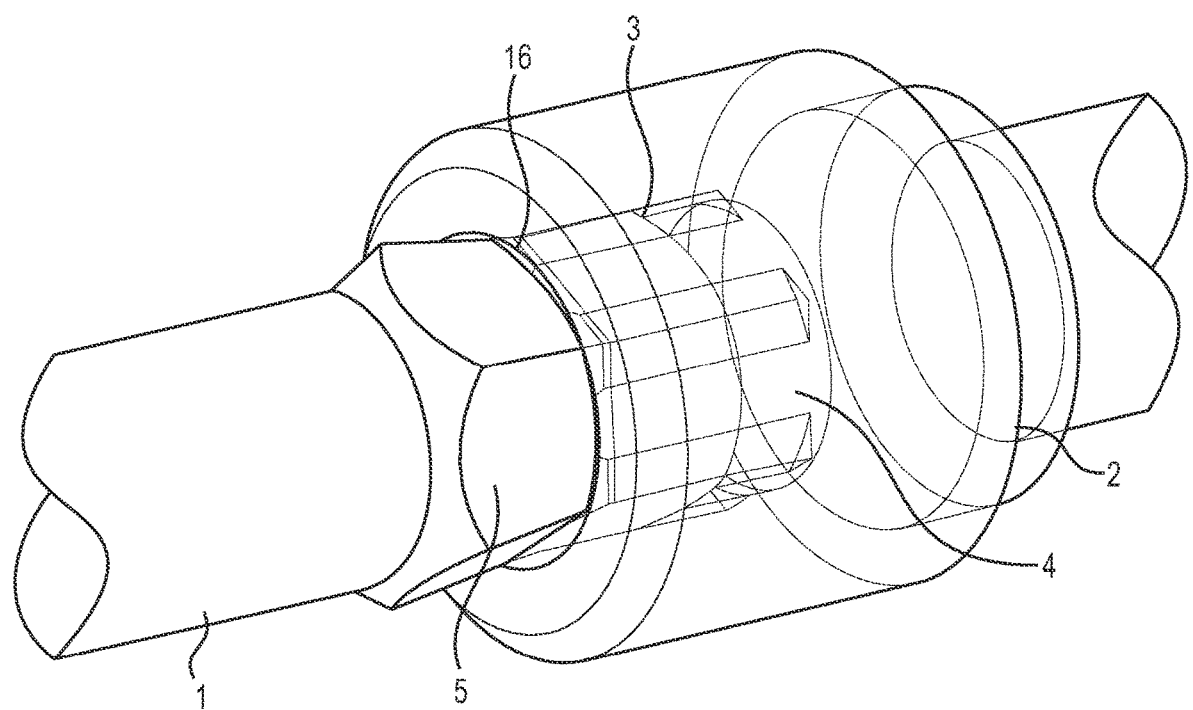
FIG. 1—perspective view of the end of a prior art hexagonal capture tool, highlighting the capture region.
Figure 2:
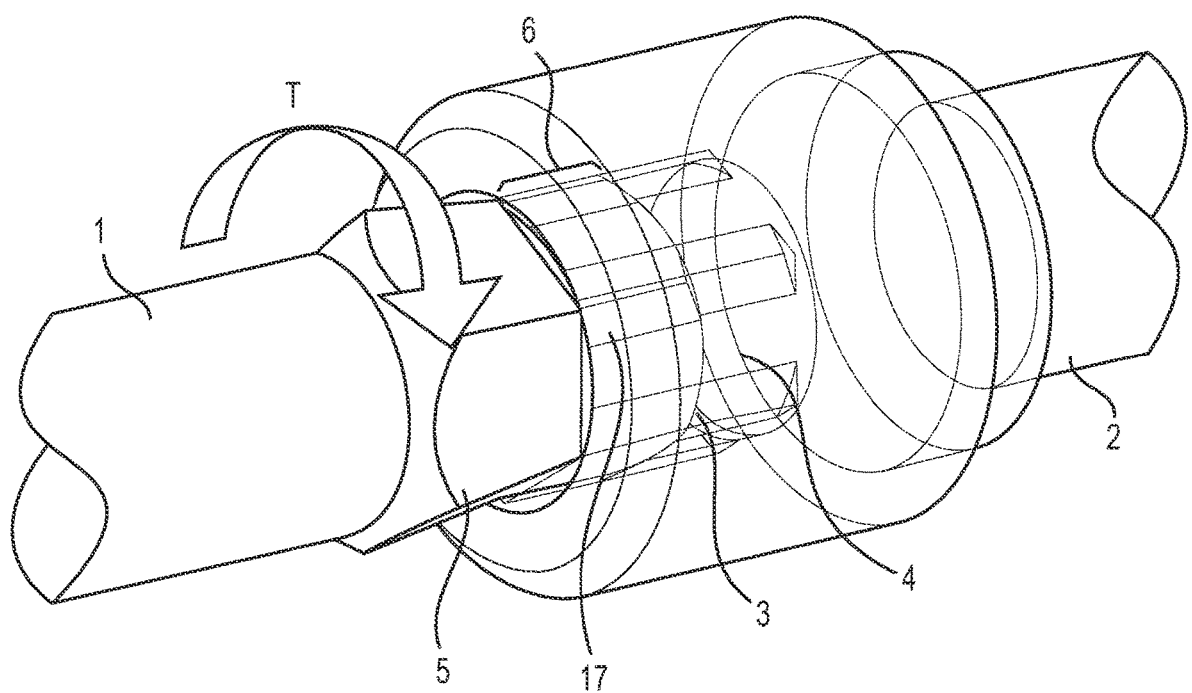
FIG. 2—perspective view of the end of a prior art capture tool, highlighting the torque region.
Figure 3:
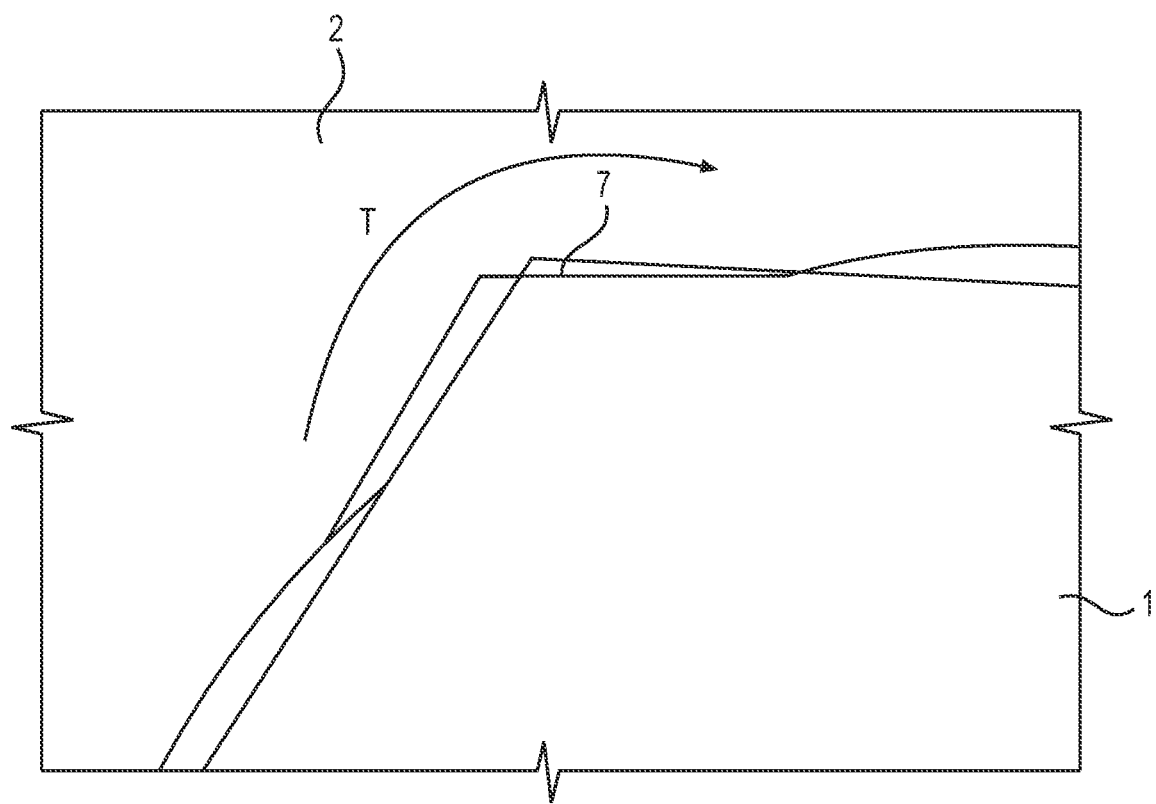
FIG. 3—sectional front view of detail A of the hexagonal tool illustrated in FIGS. 1 and 2 at the moment of torque.

FIGS. 1-3 illustrate a hexagonal tool 1 commonly used in the prior art, more specifically, a hexagonal capture tool 1 cooperating with a prosthetic component 2.

As seen in FIG. 1, the tip 3 of tool 1 is unable to fully penetrate the length of the internal orifice of component 2 due to the conical portion 5, such that the bottom region 4 of the internal orifice of component 2 does not contact the tip 3 of tool 1. This limitation occurs in regions of interference 16 highlighted in FIG. 1.

Thus, when a torque T is applied (see FIG. 2) to fasten the component 2 in the implant (not shown), note that it is only applied in the upper portion 6 of the internal orifice of component 2. The contact regions/points 17 are highlighted in said FIG. 2. This difference in torque T application makes it so that component 2 experiences deformations and, should the dentist continue to perform the fastening movement, more deformations will occur until such deformations add up and result in the deformation of the tool ridges 1, so that it will start to rotate on its own, no longer performing torque T.

Thus, the tool 1 with conical tip works only for the capture function and to provide only a first torque to lightly fasten the component 2 in the implant. In order to provide the optimal and necessary torque to fasten the component 2 in the implant, the use of a straight-tipped, non-angled tool is ideal, allowing the internal surface of component 2 to fully contact the tip 3 of tool 1, whereby the application of torque T is made preferably uniformly throughout component 2.

Furthermore, FIG. 3 shows in enlarged details that the hexagonal tool 1 has only a small contact region 7 actually in contact with the internal surface of component 2 for performing torque T. Thus, in addition to the deformations that occur through the use of tool 1 to tighten component 2, should the dentist provide a torque T greater than necessary for fastening component 2 in the implant, component 2 tends to deform with the intensity of force applied to it, i.e., the head of component 2 tends to dilate. This deformation is very common in parts small in diameter (smaller than 1.4 mm) that use smaller tools, as such tools support less torque and tend to deform more easily.

This deformation is extremely harmful, especially if component 2 needs to be removed for any reason. When the dentist uses a tool to remove the deformed component 2 (dilated head), tool 1 will have difficulty fitting in and, as a result, removing component 2.

Therefore, the present invention aims to provide a dental tool, which performs the function of capturing and fastening a prosthetic component 2 without the need to switch tools, reducing the possibility of defects in the component/screw 2 when applying torque T (dilation of screw head/component) and which can further be used on components with diameters smaller than 1.4 mm.

Figures 4A, 4B, 4C:
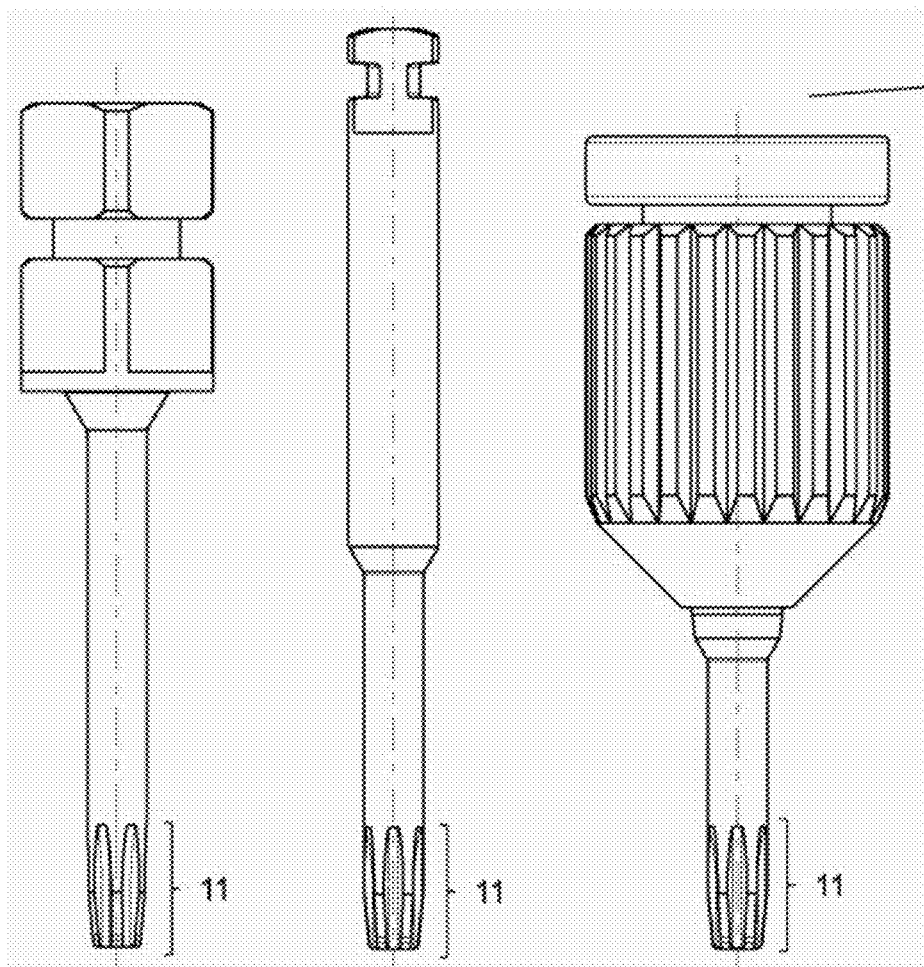
FIG. 4a—side view of a first embodiment of the dental tool herein.
FIG. 4b—side view of a second embodiment of the dental tool herein.
FIG. 4c—side view of a third embodiment of the dental tool herein.

FIGS. 4a-4c illustrate three capture and fastening tool 10 embodiments of the present invention, wherein its lower end 11 has been modified so as to solve the problems presented by the prior art.

As best seen in FIGS. 5-7b, the lower end 11 of the dental tool 10 comprises a plurality of protrusions 12, preferably six axial protrusions distributed around its circular perimeter. Said protuberances 12 are divided, from the tip 3 of end 11, into three subsequent regions; the first region 12.1 being equipped with a corner break with the function of facilitate fitting the tool in the component/screw 20; a second region 12.2 parallel to the longitudinal axis of the wrench, which will be housed inside the component; and a third region 12.3 conical/angled in shape.

Figure 5:
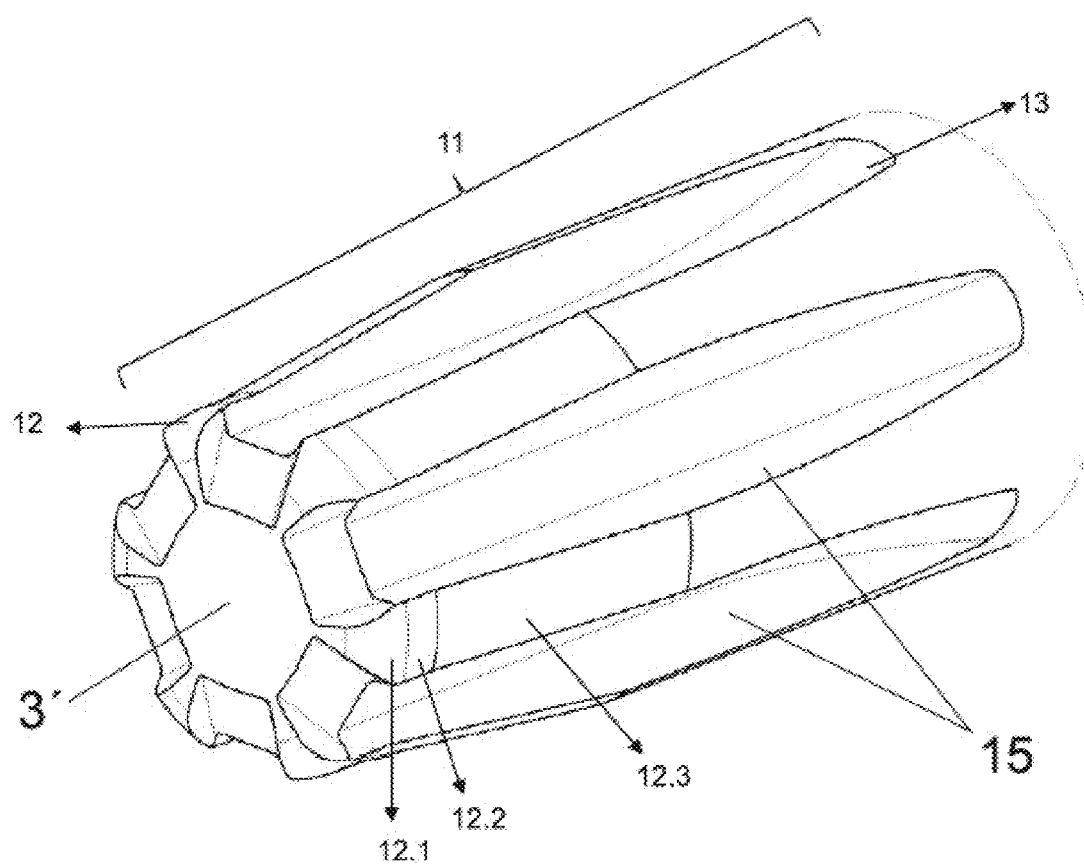
FIG. 5—perspective view of the front end of the dental tool herein.

In the embodiment illustrated in FIGS. 5, 6a and 6b the recesses 13 extend into the region next to the center of the circular end 3' of the tip 3 of the tool 10.

Figure 7B:
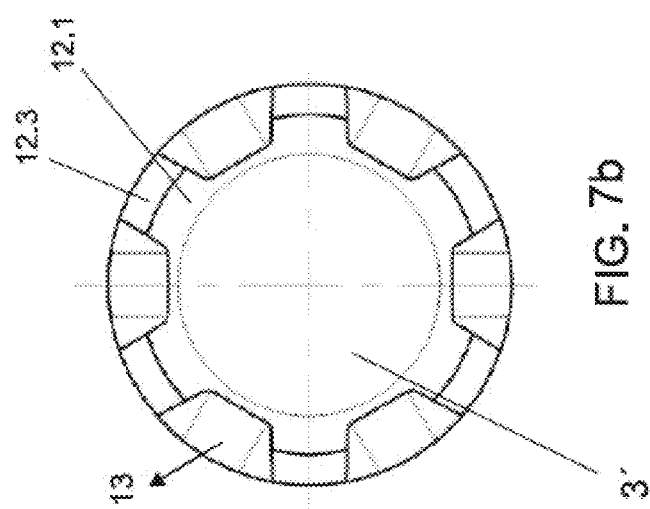
FIG. 7b—second top view of the lower end of a second embodiment of the dental tool herein.
Figure 7A:
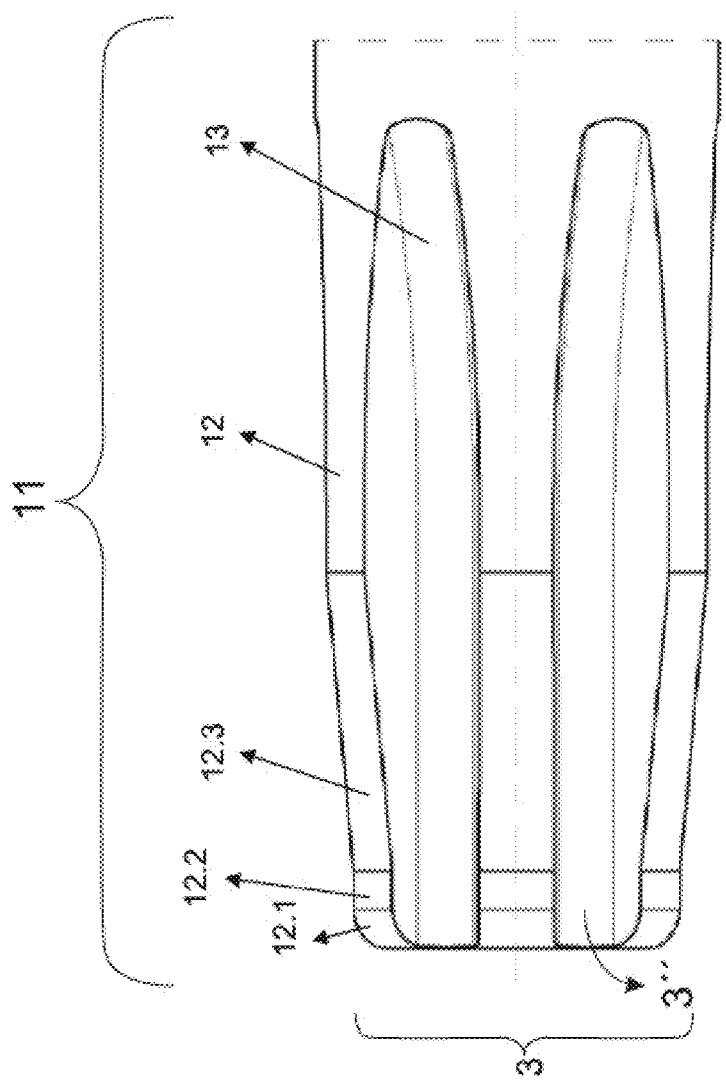
FIG. 7a—side view of the end of a second embodiment of the dental tool herein.

Optionally and as shown in FIGS. 7a and 7b, the lower end 11 of the tool 10 further comprises, alternately with the protrusions 12, a plurality of recesses 13 also axial in the circular axis of the tool 10, said recesses 13 having no extensions. Thus, in the embodiment illustrated in FIGS. 7a and 7b, the recesses 13 extend only up to an edge 3" of the tip 3 of the tool 10, not extending in proximity to the center of the circular end 3'.

This configuration allows protrusions 12 and recesses 13 to have different mechanical functions when the tool 10 is used.

Figure 8B:
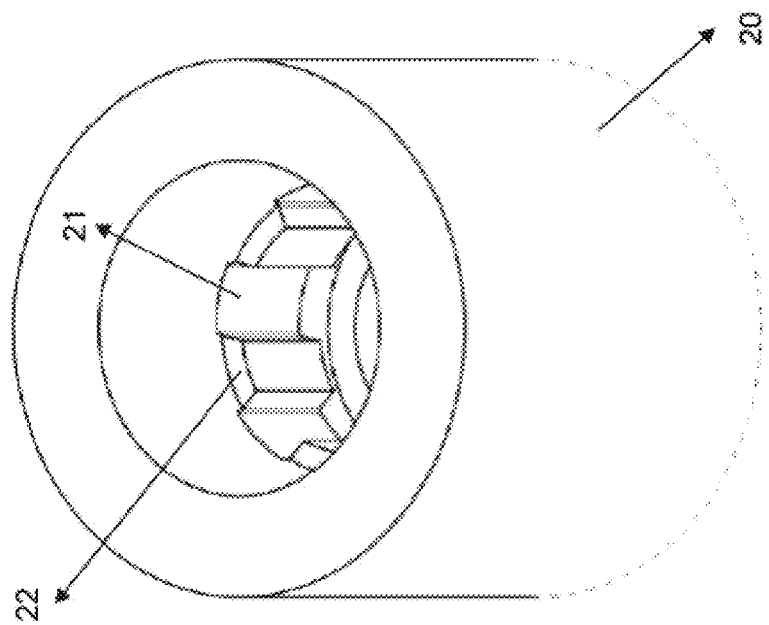
FIG. 8b—perspective view of a second embodiment of the prosthetic component/screw herein.
Figure 8A:
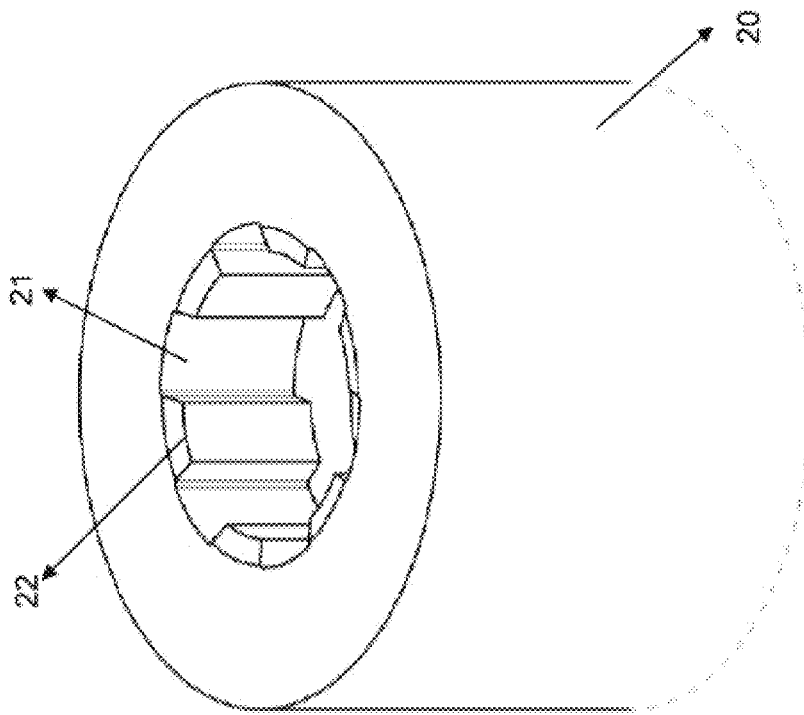
FIG. 8a—perspective view of a first embodiment of the prosthetic component/screw herein.
Figure 9A:
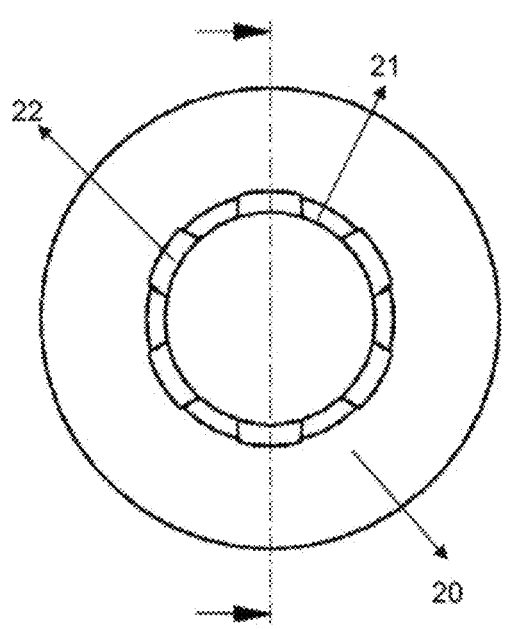
Figure 9B:
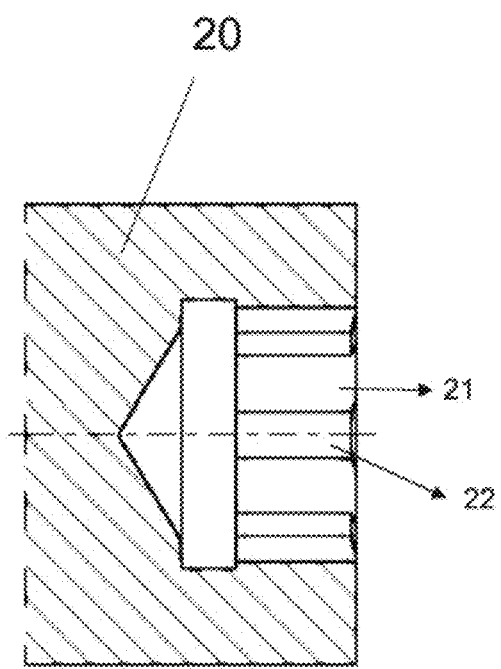

However, in order to apply the capture and fastening functions of tool 10, it is necessary to modify the components/screws 20 to better adapt to the distinct shape of the tool 10. Therefore, note in FIGS. 8a and 8b that the internal surface of the component/screw 20 is comprised of a plurality of projections 22 which form counterbores 21.

As seen in FIGS. 9a-10b, the counterbore 21 and projections 22 regions of component 20 are alternately distributed and equidistant around the inner surface of the circular section of component 20. It should be noted that in the embodiment illustrated in FIGS. 10a and 10b the internal surface of component 20 is further provided with a small settling platform 23.

Figure 11:
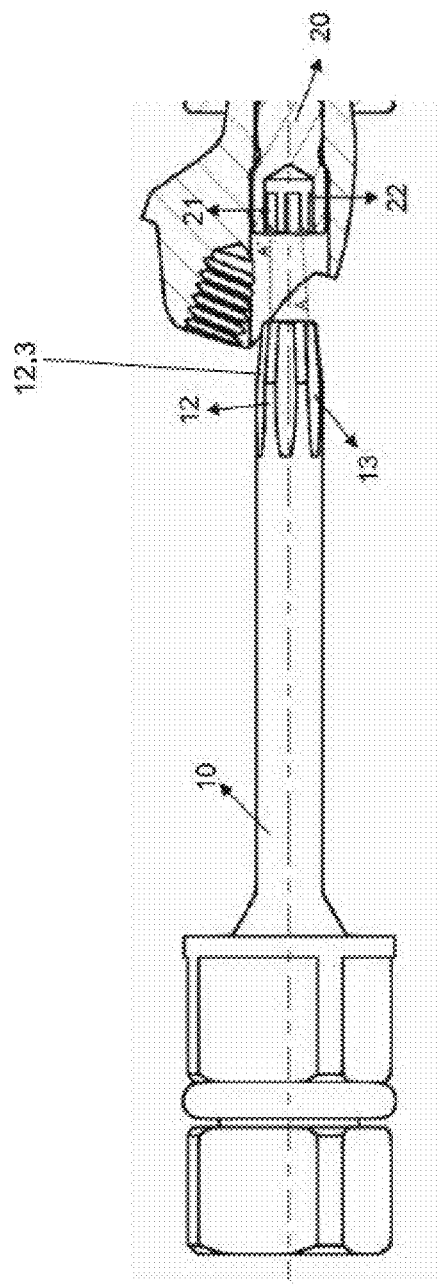
FIG. 11—partial sectional side view detailing the interaction between the dental tool with the prosthetic component/screw herein.
Figure 12:
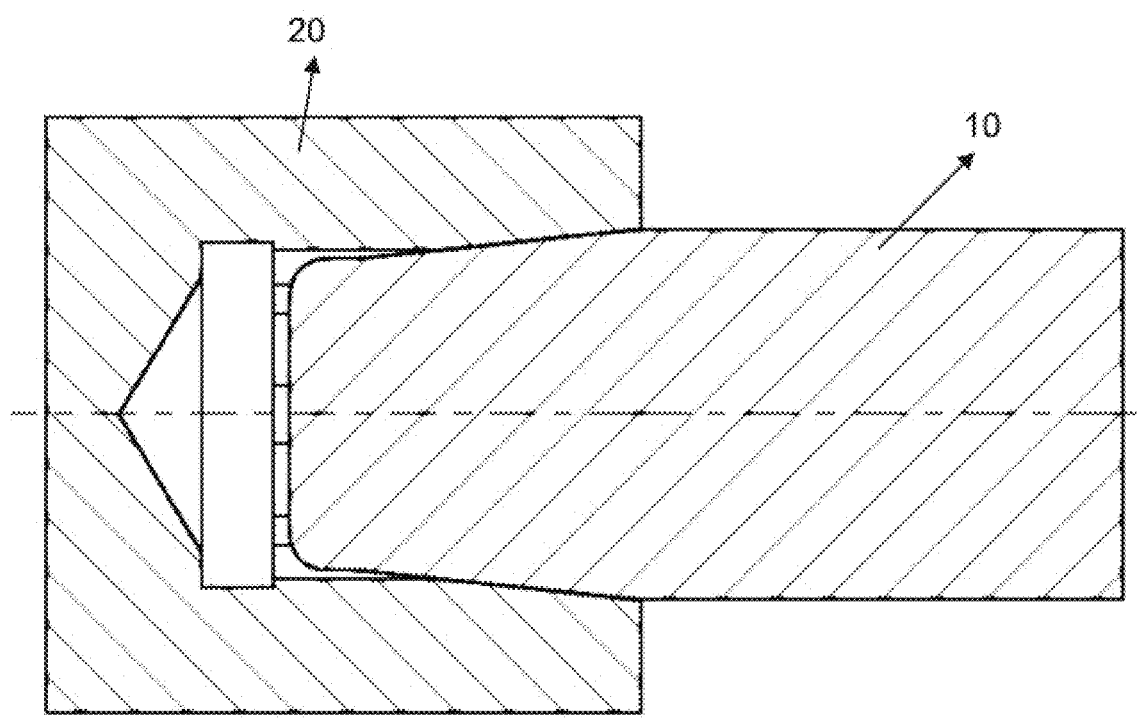
FIG. 12—sectional side view detailing the interaction between the dental tool with the prosthetic component/screw herein.

Thus, when the tool 10 is inserted into the component 20, as seen in FIGS. 11 and 12, the recesses 13 will couple with the projections 22 while the protrusions 12 will couple with the counterbores 21, as indicated by arrows A and A' in FIG. 11, respectively.

It is important to note that such modification in the shape of both tool 10 and component 20 allows the tool 10 to fully penetrate the internal extension of component 20, as the conical region 12.3 when fitting into counterbores 21 forms a flat axial fitting with the side walls of the projections 22. This avoids any tendency of defects occurring in tool 10 or component 20 when torque T is applied.

Figure 13:
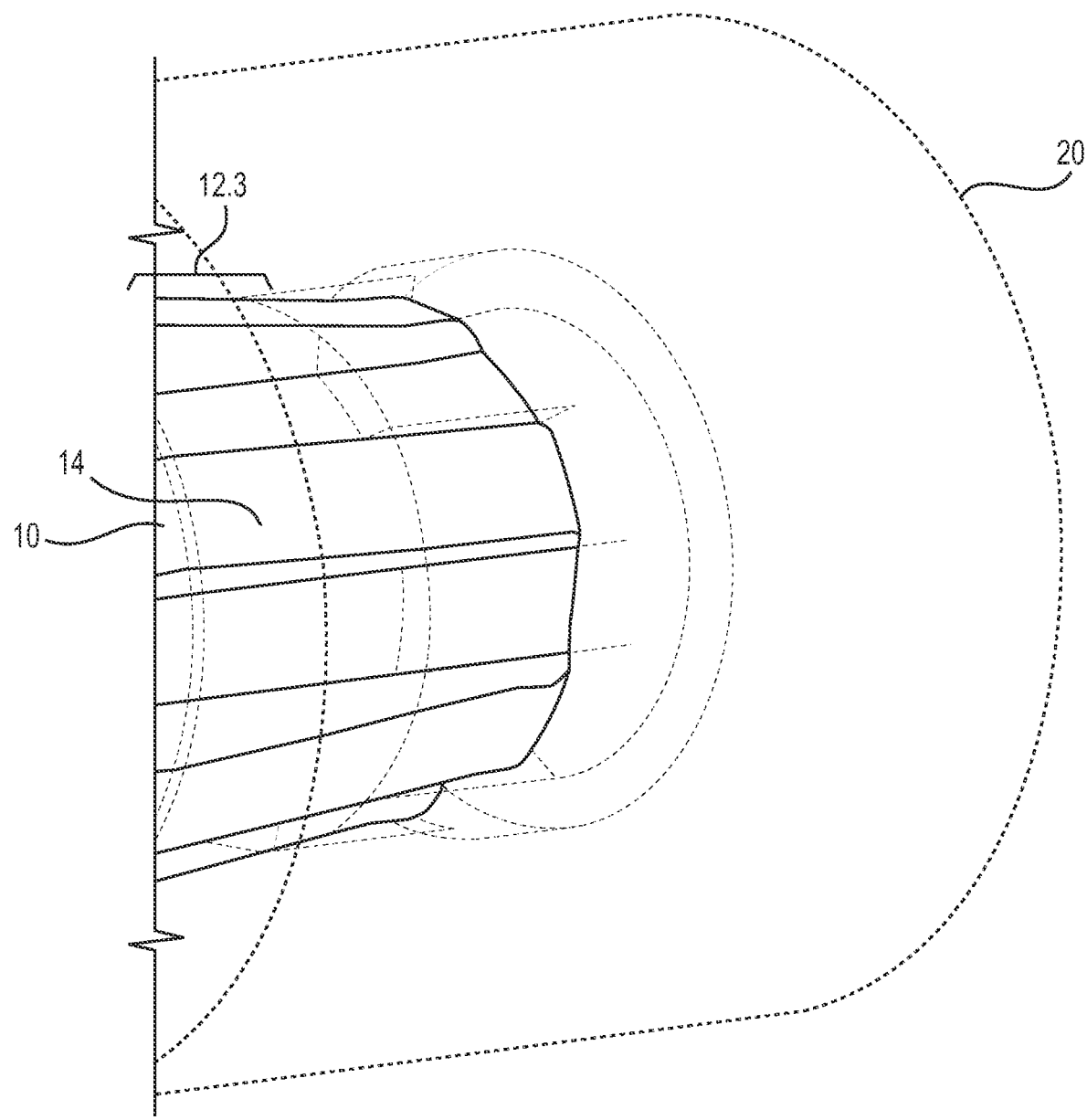
FIG. 13—perspective view of the dental tool and component/screw set herein highlighting the capture region.

With the tool 10 adequately fitted into component 20, the conical region 12.3 will function as a (retention) capture region 14 of component 20, as highlighted in FIG. 13, due to the male/female coupling formed between the conical region 12.3 and the counterbores 21 of the internal region of component 20, temporarily locking the component 20 in the tool 10. This locking allows the transportation of the component package into the installation site.

After transporting the component 20 into the installation site, the dentist needs to perform the necessary torque T to fasten it in an implant (not shown) installed at the patient's mouth.

Due to the alternate combination of the protrusions 12 and the recesses 13, side walls 15 (seen in FIGS. 7a and 14) substantially perpendicular to the longitudinal axis of the tool 10 are formed.

Figure 15A:
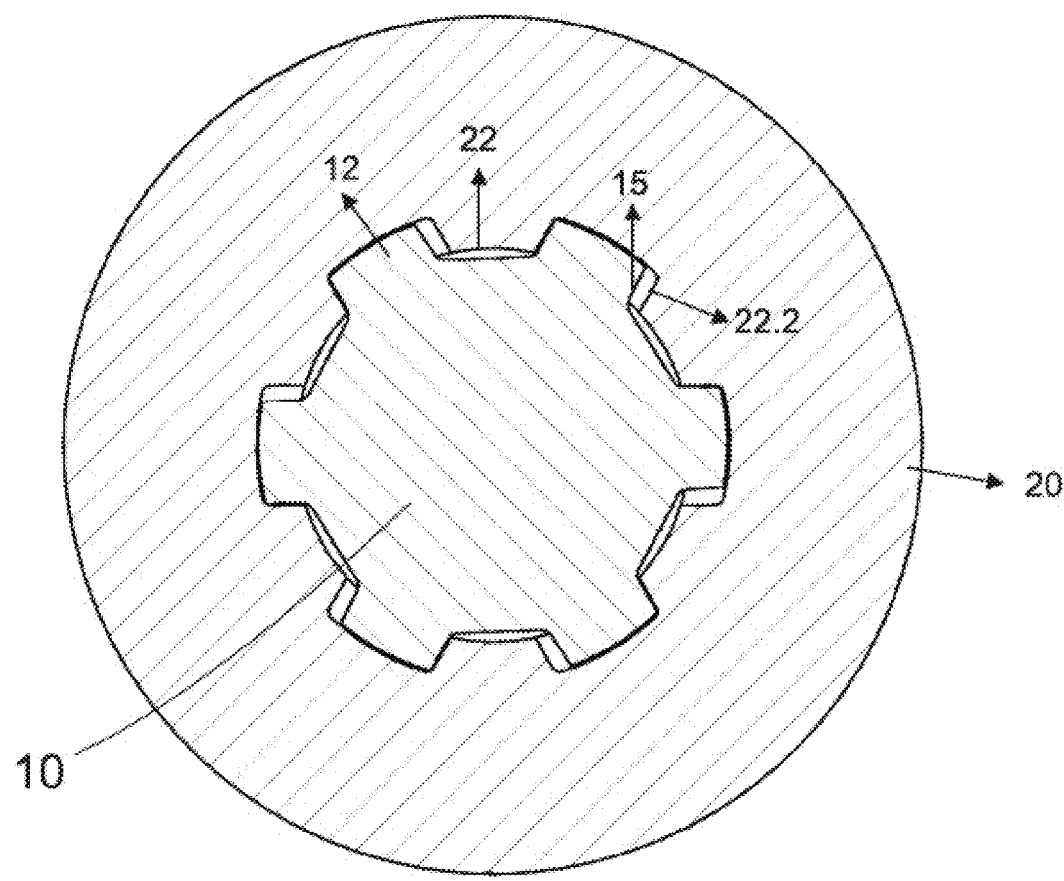
FIG. 15a—cross-sectional view detailing the interaction between the dental tool with the prosthetic component/screw herein.

Thus, when the tool 10 contacts the component 20, the side walls 15 align with side walls 22.2 substantially perpendicular to the axis of component 20, which are formed due to the alternately combination of counterbores 21 with the projections 22 (see FIG. 15a).

Figure 14:
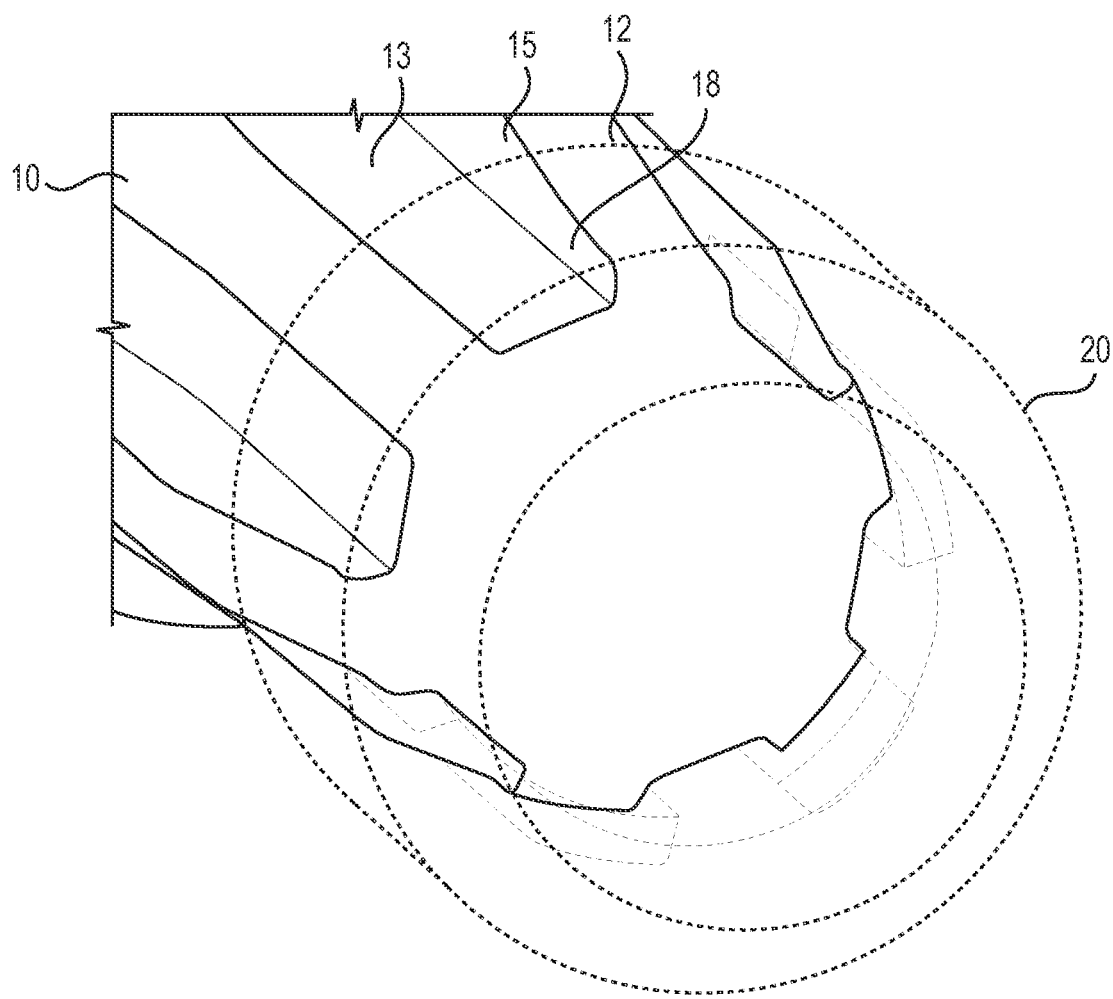
FIG. 14—perspective view of the dental tool and component/screw set herein highlighting the torque region.

Thus, when applying torque with rotation movement, the side walls 15 directly contact the entire length of the side walls 22.2 forming torque areas 18 as highlighted in FIG. 14.

Figure 15B:
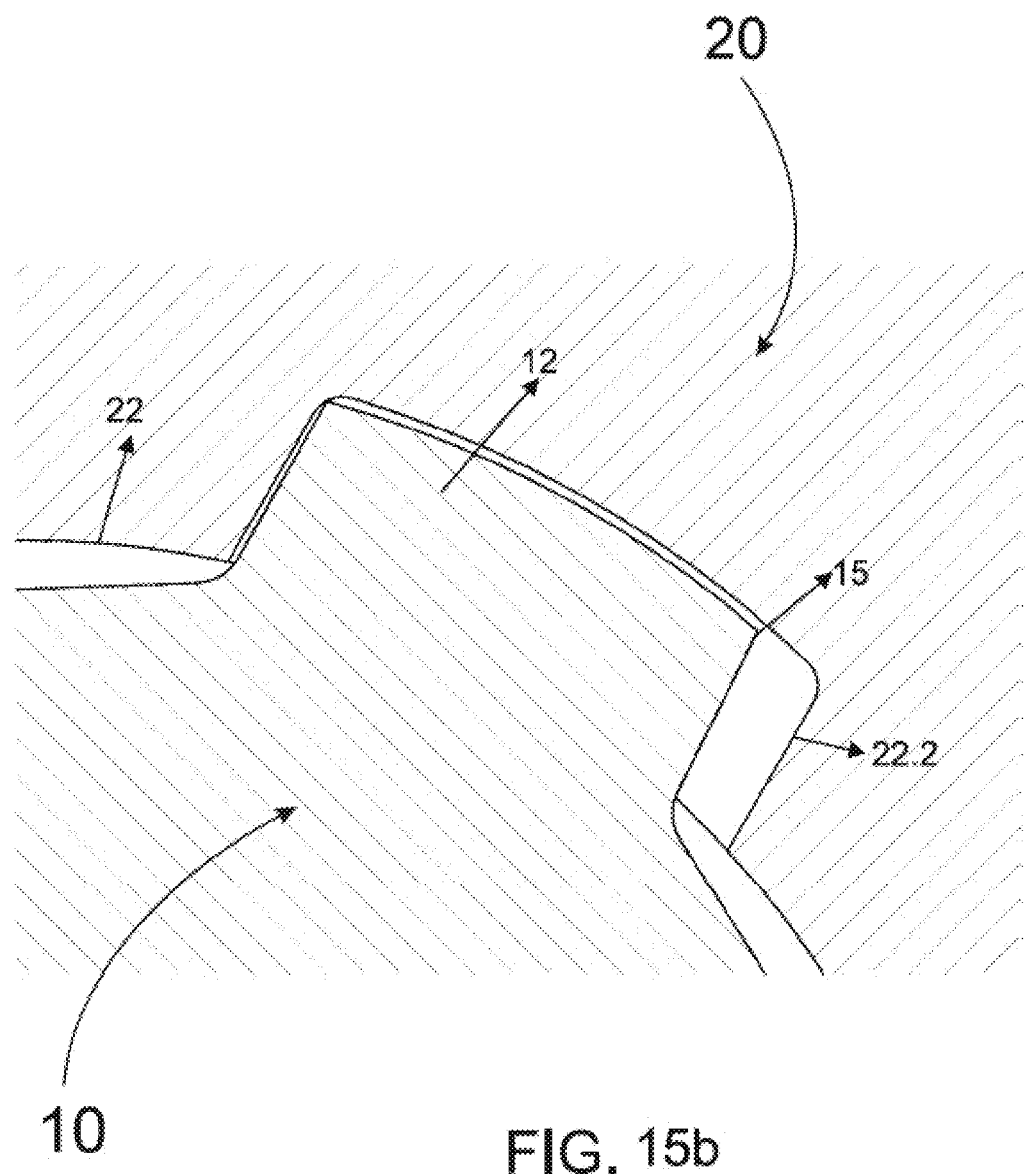

As seen in greater detail in FIGS. 15a and 15b, the point of contact for applying torque between tool 10 and component 20 does not occur at a single point, but along the entire length of the surfaces of the side wall 15, 22.2 of tool 10 and component 20, respectively.

Thus, when the dentist performs torque T to fasten the component 20 in the implant, the chances of deforming the head of the component 20 or tool 10 are significantly reduced, which reduces the chances that tool 10 will dilate the head of the component. 20 and, consequently, spin on its own and deform its ridges.

Furthermore, since the tool 10 of the present invention does not have the tendency of dilating the head of the component 20, it is possible to reduce the thickness of the wall of component 20. This decrease in wall thickness increases the fitting area of the tool 10, regardless of the size of the component 20 to be fixed.

Thus, the same tool 10 can be used for components/screws 20 of different sizes, including those with diameters smaller than 1.4 mm. This is because with the adopted geometry, the radial component of contact force between the parts is smaller, such that a smaller wall thickness is required for the same resistance with the same force applied.

Having described a preferred embodiment example, it should be understood that the scope of the present invention covers other possible variations and is limited only by the content of the appended claims, including possible equivalents thereof.

The invention claimed is:

1. A dental tool for coupling to a prosthetic component, the dental tool comprising, at a lower end:
   a plurality of protrusions, each of the plurality of protrusions extending from an edge at a distal most end of the lower end of the dental tool into three subsequent regions, the three regions being defined as:
      a first region which is (i) a circumferential corner that is convexly curved outward along a direction of a longitudinal axis of the dental tool, (ii) located at a lower tip of each respective protrusion in the direction of the longitudinal axis, and (iii) configured to facilitate fitting the dental tool into the prosthetic component,
      a second region parallel to the longitudinal axis of the dental tool, and
      a third region with a conical shape, the third region being radially tapered outward along the direction of the longitudinal axis of the dental tool away from the distal most end of the lower end of the dental tool; and
   a plurality of recesses extending to the edge at the distal most end of the lower tip of the lower end of the dental tool, wherein:
   the plurality of protrusions and the plurality of recesses are alternately arranged to form substantially flat and planar dental tool side walls which linearly and radially extend relative to the longitudinal axis of the dental tool, and
   the plurality of recesses extend to a circular flat region at the distal most end of the dental tool.

2. The dental tool according to claim 1, wherein the plurality of protrusions is six protrusions.

3. The dental tool according to claim 1, wherein the plurality of recesses is six recesses.

4. A system comprising:
   a dental tool according to claim 1; and
   the prosthetic component having an internal surface, the internal surface including:
      a plurality of counterbores, and
      a plurality of projections, wherein
         the plurality of counterbores and the plurality of projections are alternately arranged and equidistant to form component side walls that extend radially and linearly relative to a longitudinal axis of the component.

5. The system according to claim 4, wherein the internal surface further includes a settling platform.

6. The system according to claim 4, wherein:
   the plurality of protrusions are configured to engage with the plurality of counterbores,
   the plurality of recesses are configured to engage with the plurality of projections, and
   the tool side walls align with the component side walls forming torque areas.

7. The dental tool according to claim 1, wherein the first region is adjacent to the second region.

8. The dental tool according to claim 1, wherein the lower end of the dental tool is not convexly curved outward along the direction of the longitudinal axis of the dental tool at portions other than the plurality of protrusions.

9. A dental tool for coupling to a prosthetic component, the dental tool comprising, at a lower end:
   a plurality of protrusions, each of the plurality of protrusions extending from an edge at a distal most end of the lower end of the dental tool into three subsequent regions, the three regions being defined as:

a first region which is (i) a circumferential corner that is radiused, (ii) located at a lower tip of each respective protrusion in a direction of a longitudinal axis of the dental tool, and (iii) configured to facilitate fitting the dental tool into the prosthetic component, a second region entirely parallel to the longitudinal axis of the dental tool, and a third region with a conical shape that is flat and meets the second region, the third region being radially tapered outward along the direction of the longitudinal axis of the dental tool away from the distal most end of the lower end of the dental tool; and a plurality of recesses extending to the edge at the distal most end of the lower tip of the lower end of the dental tool, wherein:

the plurality of protrusions and the plurality of recesses are alternately arranged to form substantially flat and planar dental tool side walls which linearly and radially extend relative to the longitudinal axis of the dental tool, and the plurality of recesses extend to a circular flat region at the distal most end of the dental tool.

\* \* \* \* \*